(12) United States Patent
Krumhar et al.

(10) Patent No.: US 7,029,703 B2
(45) Date of Patent: *Apr. 18, 2006

(54) COMPOSITION FOR PROMOTING HEALTHY BONE STRUCTURE

(75) Inventors: Kim C. Krumhar, Carlsbad, CA (US); Holly A. Johnson, San Clemente, CA (US)

(73) Assignee: Metagenics, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/241,616

(22) Filed: Sep. 9, 2002

(65) Prior Publication Data

US 2003/0059481 A1 Mar. 27, 2003

Related U.S. Application Data

(63) Continuation of application No. 09/568,903, filed on May 11, 2000, now Pat. No. 6,447,809.
(60) Provisional application No. 60/133,603, filed on May 11, 1999.

(51) Int. Cl.
*A61K 33/42* (2006.01)
*A61K 31/351* (2006.01)
*A61K 31/59* (2006.01)
*A61K 31/592* (2006.01)
*A61K 31/593* (2006.01)
*A61K 33/00* (2006.01)
*A61K 33/06* (2006.01)
*A61K 33/22* (2006.01)
*A61K 33/24* (2006.01)
*A61P 19/00* (2006.01)

(52) U.S. Cl. ............... 424/602; 424/600; 424/617; 424/630; 424/635; 424/638; 424/639; 424/641; 424/643; 424/655; 424/656; 424/657; 424/658; 424/659; 424/660; 424/675; 424/678; 424/682; 424/683; 424/684; 424/686; 424/687; 424/688; 424/689; 424/692; 424/693; 424/694; 424/695; 424/696; 424/697; 424/724; 514/62; 514/63; 514/64; 514/167; 514/168; 514/354; 514/456; 514/457; 514/458; 514/459; 514/460; 514/492; 514/494; 514/499; 514/500; 514/505; 514/554; 514/556; 514/557; 514/561; 514/574; 514/578; 514/825

(58) Field of Classification Search ............... 424/600, 424/602, 617, 630, 635, 638–639, 641, 643, 424/655–660, 675, 678, 682–684, 686–689, 424/692–697, 724; 514/62–64, 167–168, 514/354, 456–460, 492, 494, 499, 500, 505, 514/554, 556, 557, 561, 574, 578, 825
See application file for complete search history.

(56) References Cited

OTHER PUBLICATIONS

Medline abstract, accession No. 2001449820 (2001).*
Medline abstract, accession No. 2001608214 (2001).*
Medline abstract, accession No. 92236913 (1992).*
Promt Abstract, accession No. 1988:470186 (Aug. 1998).*
Promt Abstract, accession No. 1999:105772 (Feb. 22, 1999).*
Hendler, Sheldon S. The Complete Guide to Anti–Aging Nutrients. Simon and Schuster, NY, 1985, pp. 293–300.*
Cranney, A., et al., "Responsiveness of Endpoints in Osteoporosis Clinical Trials—An Update," *The Journal of Rheumatology* vol. 26(1), pp. 222–228 Jan. 1999.
Chemical Abstracts 122:45482n., 1995.
PINNA–CAL. Product description [online] Twinlab, Date unavailable [retrieved from Internet on May 13, 2002] URL: http://shop.store.yahoo.com/twinlabproducts/0026.html.
Calcium Complex. Product description [online]. Natural Ways to Health, date unavailable, Retrieved from Internet on May 13, 2002] URL: http://WWW.NATURALWAYS.COM/Calcium.htm.
Nutritional Supplements Cal Apatite Plus™ Product description [online] Arthritis Center of Riverside, date unavailable [Retrieved from Internet on May 13, 2002. URL: http://WWW.THE ARTHRITISCENTER.COM/CAPLUS.HTM.
PINNA–CAL. World Mark [Retrieved on line from Internet on May 17, 2002 URL:http://tess.USPTO.gov/bin/showfield? f=doc&state=d9eer0.2.1. Jul. 1999.
I.R. Reid, et al., *Prophylaxis Against Vitamin D Deficiency in the Elderly by Regular Sunlight Exposure*, vol. 15, Age and Ageing, 35–40, 1986.
D. Agnusdei, et al., *Metabolic and Clinical Effects of Ipriflavone in Established Post–Menopausal Osteoporosis*, vol. 15, No. 2, Drug Exptl. Clin. Res, 97–104, 1989.
A. Pines, et al., *Clinical trail of microcrystalline hydroxyapatite compound ('Ossopan') in the prevention of osteoporosis due to corticosteroid therapy*, vol. 8, No. 10, Current Medical Research and Opinion, 734–742, 1984.

(Continued)

*Primary Examiner*—John Pak
(74) *Attorney, Agent, or Firm*—McDermott Will & Emery LLP

(57) ABSTRACT

A dietary supplement for benefitting human bone health includes a calcium source, a source of vitamin D activity, and an osteoblast stimulant. A preferred calcium source is microcrystalline hydroxyapatite, which also contains protein (mostly collagen), phosphorus, fat, and other minerals. A preferred source of vitamin D activity is cholecalciferol, and a preferred osteoblast stimulant is ipriflavone. In addition to these basic ingredients, the composition can further include various other minerals known to occur in bone, vitamin C, and glucosamine sulfate, all of which exert beneficial effects on growth and maintenance of healthy bone. A method for benefitting human bone health involves administering a daily regimen of the dietary supplement.

24 Claims, No Drawings-

OTHER PUBLICATIONS

Jan. J. Stepan, et al., *Quantitation of Growth Factors in Ossein–Mineral–Compound*, vol. 49, Life Sciences, PL–79—PL–84, 1991.

M. Annefeld, et al., *The influence of ossein–hydroxyapatite compound ('Ossopan') on the healing of a bone defect*, vol. 10, Current Medical Research Opinion, 241–250, 1986.

Lisa G. Abbott, et al., *Clinical Manifestations of Magnesium Deficiency*, vol. 19, Miner Electrolyte Metab, 314–322, 1993.

D. R. Fraser, *Vitamin D*, vol. 345, The Lancet, 104–107, Jan. 14, 1995.

Marcel E. Ooms, et al., *Prevention of Bone Loss by Vitamin D Supplementation in Elderly Women: A Randomized Double–Blind Trial*, vol. 80, No. 4, Journal of Clinical Endocrinology and Metabolism, 1052–58, 1995.

G.B. Melis, et al., *Lack of any estrogenic effect of ipriflavone in postmenopausal women*, vol. 15, Journal of Endocrinology Invest, 755–761, 1992.

T. Ushiroyama, et al., *Efficacy of ipriflavone and 1 α vitamin D therapy for the cessation of vertebral bone loss*, vol. 48, International Journal of Gynecology & Obstetrics, 283–88, 1995.

Attila B. Kovács, *Efficacy of ipriflavone in the prevention and treatment of postmenopausal osteoporosis*, vol. 41, Agents Actions, 86–87, 1994.

M. Valente, et al., *Effects of 1–Year Treatment with Ipriflavone on Bone in Postmenopausal Women with Low Bone Mass*, vol. 54, Calcified Tissue International, 377–380, 1994.

Owen Epstein, et al., *Vitamin D hydroxyapatite, and calcium gluconate in treatment of cortical bone thinning in postmenopausal women with primary biliary cirrhosis*, vol. 36, The American Journal of Clinical Nutrition, 426–30, Sep. 1982.

P. Rüegsegger, et al., *Comparison of the Treatment Effects of Ossein–Hydroxyapatite Compound and Calcium Carbonate in Osteoporotic Females*, vol. 5, Osteoporosis International, 30–34, 1995.

D. Agnusdei, et al., *Effects of ipriflavone on bone mass and calcium metabolism in postmenopausal osteoporosis*, vol. 19, Bone and Mineral, S43–48, 1992.

D. Agnusdei, et al., *Efficacy of Ipriflavone in Established Osteoporosis and Long–Term Safety*, vol. 61, Calcified Tissue International, S23–27, 1997.

Paul D. Saltman, et al., *The Role of Trace Minerals in Osteoporosis*, vol. 12, No. 4, Journal of the American College of Nutrition, 384–89, 1993.

S. Adami, et al., *Ipriflavone Prevents Radial Bone Loss in Postmenopausal Women with Low Bone Mass over 2 years*, vol. 7, Osteoporosis International, 119–125, 1997.

Jean–Yves L. Reginster, *Ipriflavone: pharmacological properties and usefulness in postmenopausal osteoporosis*, vol. 23, Bone and Mineral, 223–232, 1993.

\* cited by examiner

COMPOSITION FOR PROMOTING HEALTHY BONE STRUCTURE

CROSS-REFERENCE TO RELATED APPLICATIONS

This application is a continuation of application Ser. No. 09/568,903, filed May 11, 2000, now U.S. Pat. No. 6,447,809, which claims the benefit of U.S. Provisional Application No. 60/133,603, filed May 11, 1999, which is hereby incorporated herein by reference.

BACKGROUND OF THE INVENTION

This invention relates to dietary supplements. More particularly, this invention relates to compositions and methods for promoting healthy bone structure.

Osteoporosis is a common metabolic bone disease that leads to the gradual loss of mineralized bone from the skeletal mass. This is due in part to an imbalance in the rates of cell-mediated bone deposition and resorption due to the actions of osteoblasts and osteoclasts in the bone matrix. Bone mineral is in a constant state of destruction and repair referred to as "remodeling," and maintenance of bone density over time is believed to require a precise balance after menopause or during the course of certain disease states. Bone resorption, when exceeding bone formation, can lead to bone fractures resulting from minimal trauma. Unfortunately, there are no symptoms preceding fractures. A common cause of osteoporosis is the decrease in estrogen production following menopause that leads to an increase in bone resorption. Conventional methods to counter bone resorption in women include estrogen therapy and calcium supplementation. Long-term treatment with estrogen has been the only method correlated to significant protection from bone loss in postmenopausal women. See Agnusdei D, Bufalino L. Efficacy of ipriflavone in established osteoporosis and long-term safety. Calcified Tissue International 1997; 61:S23–S27. The isoflavone, ipriflavone, is now successfully used in many countries to treat and prevent osteoporosis.

Ipriflavone (7-isopropoxyisoflavone) was discovered in 1969 by investigators in Budapest while studying plant growth factors. They found that ipriflavone modulates the oxidative phosphorylation mechanisms at the mitochondrial level and subsequently improved cellular oxygen consumption. Later research demonstrated that ipriflavone can increase calcium, phosphorus, and potassium retention in humans, see Agnusdei D, Zacchei F, Bigazzi S, et al. Metabolic and clinical effects of ipriflavone in established postmenopausal osteoporosis, Drugs Exp Clin Res 1989; (XV)2:97–104), and reduce bone turnover rate by inhibiting bone resorption (osteoclasts), see Agnusdei D, Bufalino L. Efficacy of ipriflavone in established osteoporosis and long-term safety. Calcified Tissue International 1997; 61:S23–S27 and Gennari C, Adanii S, Agnusdei D., et al. Effect of chronic treatment with ipriflavone in postmenopausal women with low bone mass, Calcif. Tissue Int. 1997; 61:SI9–S22. Numerous double-blind, placebo-controlled studies have shown a positive effect of ipriflavone in reducing bone mineral loss and increasing bone density in postmenopausal women with osteopenia or established osteoporosis at a dose of 600 mg/day, see Adami S, Bufalino L, Cervetti R, et al., Ipriflavone prevents radial bone loss in postmenopausal women with low bone mass over 2 years, Osteoporosis Int 1997; 7:119–25; Valente M, Bufalino L, Castiglione G N, et al., Effects of 1-year treatment with ipriflavone on bone in postmenopausal women with low bone mass, Calcif. Tissue Int. 1994; 54:377–380; Agnusdei D, Camporeale A, Gonnelli S, et al. Short-term treatment of Paget's disease of bone with ipriflavone, Bone Miner. 1992; 19: (Suppl) S35–S42, Agnusdei D, Zacchei F, Bigazzi S, et al., Metabolic and clinical effects of ipriflavone in established postmenopausal osteoporosis, Drugs Exp Clin Res 1989; (XV)2:97–104; Agnusdei D, Bufalino L., Efficacy of ipriflavone in established osteoporosis and long-term safety, Calcified Tissue International 1997; 61:S23–S27; Kovacs A B, Efficacy of ipriflavone in the prevention and treatment of postmenopausal osteoporosis, Agents Actions 1994; 41:86–7; Passeri, M, Biondi M, Costi D, et al., Effect of ipriflavone on bone mass in elderly osteoporotic women, Bone Miner. 1992: 19: (Suppl) S57–S62.

In these studies, all patients received an oral calcium supplement of 1 g/day in addition to ipriflavone or placebo. One of the researchers, Dr. Donato Agnusdei, stated that "long-term treatment with ipriflavone may be considered safe, and may increase bone density and possibly prevent fractures in elderly patients with established osteoporosis" Agnusdei D, Bufalino L., Efficacy of ipriflavone in established osteoporosis and long-term safety, Calcified Tissue International 1997; 61:S23–S27. Another study evaluating the effects of ipriflavone combined with vitamin D showed that the combined therapy was more effective in reducing bone loss than either therapy alone or control. Ushiroyama T, Okamura S, Ikeda, A, et al., Efficacy of ipriflavone and 1-alpha vitamin D therapy for the cessation of vertebral bone loss, Int J Gynecol Obstet 1995; 48:283–8. A double-blind placebo controlled study of 28 osteoporotic elderly women (having at least one vertebral fracture) taking 600 mg ipriflavone/day along with 1 gram calcium showed a 6% increase ($P<0.05$) in BMD at the distal radius (DPA). See Passeri, M, Biondi M, Costi D, et al., Effect of ipriflavone on bone mass in elderly osteoporotic women, Bone Miner. 1992: 19: (Suppl) S57–S62. Urinary hydroxyproline/creatinine (HOP/Cr) and serum osteocalcin (BGP) were also reduced in the ipriflavone treated group. Compliance with the oral administration of ipriflavone was good.

All clinical trials confirm a very good tolerance of ipriflavone with a frequency of adverse reactions equal to that observed during administration of a placebo. Despite its structural similarity with some naturally occurring phytoestrogens, ipriflavone has been shown to be devoid of any estrogenic activity in animals and in humans and does not appear to modify secretion or metabolism of endogenous estrogens. See Valente M, Bufalino L, Castiglione G N, et al., Effects of 1-year treatment with ipriflavone on bone in postmenopausal women with low bone mass, Calcif Tissue Int 1994; 54:377–380 and Melis G B, Paoletti A M, Cagnacci A, et al., Lack of any estrogenic effect of ipriflavone in postmenopausal women, J Endocrinol Invest 1992; 15:755–61.

A preliminary cross over (600/1200 mg ipriflavone vs. 1200/600 mg ipriflavone) 30 day study of patients with Paget's disease indicated that ipriflavone supplementation prevented the loss of bone through the inhibition of bone resorption. See Agnusdei D, Camporeale A, Gonnelli S, et al., Short-term treatment of Paget's disease of bone with ipriflavone, Bone Miner. 1992; 19: (Suppl) S35–S42. Following the 1200/600 mg ipriflavone sequence, biochemical measures of bone resorption were affected significantly. Serum alkaline phosphatase (ALP) decreased 33% ($P<0.01$) and hydroxy proline/creatinine (HOP/Cr) decreased 24.1% ($P<0.05$). Bone pain was significantly decreased in patients during the 1200/600 mg sequence of ipriflavone. The analgesic effect was rapid and independent of ipriflavone action or bone turnover. The pain relief mechanism is unknown at this time. Id.

A sub-optimal vitamin D status diminishes the production of 1,25-dihydroxyvitamin D (1,25-$(OH)_2$D), which is required for calcium to be actively absorbed in the intestine as well as the homeostatic treatment of calcium by the kidney. See Fraser D R., Vitamin D, The Lancet 1995; 345:104–107. The inadequate absorption will lead to secondary hyperparathyroidism resulting in increased bone resorption and cortical bone loss. Vitamin D status has been correlated with bone mineral density (BMD) of the proximal femur and vertebrae. Supplementation with 1 cc vitamin D increases serum 1,25-$(OH)_2$D levels, increases intestinal calcium absorption, and decreases the secretion of parathyroid hormone (PTH). One study found that elderly women receiving 400 IU 1α vitamin D for one year significantly increased serum 25-hydroxyvitamin D and 1,25-dehydroxyvitamin D, increased BMD at the femoral neck, and significantly decreased PTH. See Ooms M E, Roos J C, Bezemer P D, Van der Vijgh W J, Bouter, L M, Lips P., Prevention of bone loss by 1α vitamin D supplementation in elderly women: a randomized double-blind trial, Journal of Clinical Endocrinology and Metabolism 1995; 80(4):1052–1058. Another short study concluded that IP inhibited bone resorption without affecting bone formation in patients with primary hyperparathyroidism. Mazzouli G F, Romagnoli E, Camevali V, Scarda A, Scamecchia M, Pacitti M T, Rosso R, Minisola V., Effects of ipriflavone on bone modeling in primary hyperparathyroidism, Bone Miner. 1992; 19:S27–S33. The women were supplemented with 1200 mg ipriflavone daily divided in three doses.

Adequate calcium ingestion and absorption is crucial for the maintenance of bone mass. Research indicates that the presence of other food components with elemental calcium greatly increases absorption. Ossein-mineral-compound prepared from calf bone powder has been shown to increase calcium absorption (as compared to synthetic microcrystalline hydroxyapatite) and contains proteins that are mitogenic for bone cells in vitro. See Stepan J J, Mohan S, Jennings J C, et al., Quantitation of growth factors in ossein-mineral-compound, Life Sciences 1991; 49:79–84. Microcrystalline hydroxyapatite from raw whole bone also contains the minerals phosphorus, magnesium, fluoride, zinc, silicon, manganese, copper, and other trace minerals that are physiologically involved in bone formation and metabolism. Trace minerals have catalytic functions (important as cofactors for the proper functioning of specific enzymes) in organic bone matrix that are crucial for the normal development and maintenance of skeletal tissue. See Strause et al., The role of trace elements in bone metabolism, Nutritional Aspects of Osteoporosis, New York: Raven Press; 1991(Strause, 1991). When calcium carbonate and microcrystalline hydroxyapatite were compared for effectiveness in preventing further bone loss in postmenopausal osteoporosis, the calcium carbonate reduced the rate of bone loss by about half, while the microcrystalline hydroxyapatite was shown to nearly halt it. See Seelig M S, Prophylactic treatment of osteoporosis with estrogen and calcium increases need for magnesium, J Am Coll Nutr 1989; 8:457A. Another study of osteoporotic postmenopausal women, with the complication of primary biliary cirrhosis, showed that MCHC supplementation not only helped reduce bone loss but it actually helped increase cortical bone thickness by 6.1%. Abbott L G, Rude R K, Clinical manifestations of magnesium deficiency, Miner Electrolyte Metab 1993; 19:314–322. While prior art formulas as dietary supplements containing calcium or 1α vitamin D or ipriflavone are known and are generally suitable for their limited purposes, they possess certain inherent deficiencies that detract from their overall utility in providing maximal protection against bone loss and maximal increases in bone mass. For example, a dietary supplement containing calcium and 1α vitamin D will increase absorption and utilization of calcium within the body; such a supplement does not offer the benefits of decreased bone resorption that will occur with ipriflavone in accordance with the present invention. Furthermore, a dietary supplement containing ipriflavone alone will not offer the benefits of increases in dietary calcium, other minerals, and vitamins important for bone health. Prior art formulas fail to provide all the components necessary to provide maximal availability of, absorption of, and utilization of, vitamins and minerals essential to optimal bone health in addition to components that decrease bone resorption and increase bone density through increased retention of minerals within the bone.

In view of the foregoing, it will be appreciated that a composition for maximally improving and maintaining bone mass density by providing highly bioavailable calcium, organic bone matrix shown to contain proteins that are mitogenic for bone cells in vitro, a full complement of minerals in the same physiological proportions found in healthy bone to include phosphorus, magnesium, fluoride, zinc, silicon, manganese, and other trace minerals, 1α vitamin D, in addition to components shown to inhibit bone resorption and stimulate bone formation would significantly advance the art.

OBJECTS AND SUMMARY OF THE INVENTION

It is an object of the present invention to provide a composition for use as a dietary supplement that benefits human bone health with oral administration.

It is also an object of the invention to provide a composition for use as a dietary supplement that, when ingested, is effective for reducing and/or halting the rate of bone loss or bone thinning associated with osteoporosis and possibly increasing bone density.

It is another object of the invention to provide a composition for use as a dietary supplement that, when ingested, will reduce bone turnover rate by inhibiting bone resorption while increasing the retention of calcium, phosphorus, and potassium in the human body.

It is another object of the invention to provide a composition for use as a dietary supplement that, when ingested, provides the mineral, calcium, in a very bioavailable form while also providing phosphorus, magnesium, and trace minerals in the physiological proportions found in healthy bone, in addition to the organic matrix in healthy raw bone which includes collagen and noncollagenous proteins/peptides with active growth factors and mucopolysaccharides. See Ruegsegger P, Keller A, Dambacher M A, Comparison of the treatment effects of ossein-hydroxyapatite compound and calcium carbonate in osteoporotic females, Osteo Int 1995; 5:30–34.

It is a further object of the invention to provide a composition for use as a dietary supplement that, when ingested, improves calcium absorption and homeostatic regulation of calcium by the kidney.

It is a further object of the invention to provide ipriflavone in its most bioavailable form together with a calcium source, fat, emulsifier, and vitamin D in the form of a dehydrated emulsion, which is reconstituted to an oil-in-water emulsion when hydrated in the stomach or other aqueous environment.

These and other objects can be addressed by providing a composition for benefitting human bone health comprising an admixture of:

(a) an effective amount of a calcium source;
(b) an effective amount of a source of vitamin D activity; and
(c) an effective amount of an osteoblast stimulant.

Preferably, the calcium source comprises microcrystalline hydroxyapatite present in the range from about 100 mg to about 5000 mg, the source of vitamin D activity comprises cholecalciferol present in the range from about 50 IU to about 300 IU, and the osteoblast stimulant comprises ipriflavone present in the range from about 10 mg to about 600 mg. In another preferred embodiment of the invention the composition further comprises dicalcium phosphate present in the range from about 100 mg to about 1400 mg. In still another preferred embodiment the composition further comprises about 50 to about 400 mg of a magnesium source selected form the group consisting of magnesium oxide, magnesium glycinate, magnesium citrate, magnesium aspartate, magnesium malate, and mixtures thereof. In yet another preferred embodiment the composition further comprises about 0.04 mg to about 5 mg of a copper ingredient selected from the group consisting of copper sulfate, copper oxide, copper glycinate, copper lysinate, copper tyrosinate, copper gluconate, and mixtures thereof. In a still further preferred embodiment the composition further comprises about 1 mg to about 15 mg of a zinc ingredient selected from the group consisting of zinc sulfate, zinc oxide, zinc ascorbate, zinc glycinate, zinc aspartate, zinc arginate, zinc citrate, zinc gluconate, zinc picolinate, and mixtures thereof. Another preferred embodiment of the invention further comprises about 0.5 mg to about 10 mg of a manganese ingredient selected from the group consisting of manganese sulfate, manganese glycinate, manganese gluconate, manganese arginate, manganese aspartate, and mixtures thereof. Still another preferred embodiment of the invention further comprises about 0.1 mg to about 4 mg of a boron ingredient selected from the group consisting of boron citrate, boron aspartate, boron glycinate, and mixtures thereof. Yet another preferred embodiment of the invention further comprises about 1.0 mg to about 20 mg of a silicon ingredient selected from the group consisting of silicon dioxide, *Equistetum arvense*, and mixtures thereof. Another preferred embodiment of the invention further comprises about 100 mg to about 1000 mg of glucosamine sulfate. Still another preferred embodiment of the invention further comprises about 50 µg to about 300 µg of a chromium ingredient selected from the group consisting of dinicotinate glycinate, chromium aspartate, chromium picolinate, and mixtures thereof. A still further embodiment of the invention further comprises about 100 mg to about 1000 mg of a vitamin C ingredient selected from the group consisting of ascorbic acid, calcium ascorbate, sodium ascorbate, and mixtures thereof.

A method for supplementing a diet for benefitting human bone health comprises administering at least one daily serving of a composition comprising an admixture of:

(a) an effective amount of a calcium source;
(b) an effective amount of a source of vitamin D activity; and
(c) an effective amount of an osteoblast stimulant.

Additional embodiments of this method comprise administering this composition containing additional ingredients as set forth in the above summary of the composition.

Another composition for benefitting human bone health comprises an admixture of:

(a) about 10 to $600 \times 10^{-3}$ parts by weight of ipriflavone;
(b) about 20 to 500 international units of vitamin D; and
(c) about 100 to $5000 \times 10^{-3}$ parts by weight of a calcium source.

Preferably, this composition comprises about 100 to $600 \times 10^{-3}$ parts by weight of ipriflavone, about 50 to 300 international units of vitamin D, and/or about 1000 to $5000 \times 10^{-3}$ parts by weight of a calcium source. The calcium source can comprise microcrystalline hydroxyapatite, dicalcium phosphate, and mixtures thereof. Another preferred embodiment of the invention further comprises about 50 to $400 \times 10^{-3}$ parts by weight of magnesium, about 0.04 to $5 \times 10^{-3}$ parts by weight of copper, about 1 to $15 \times 10^{-3}$ parts by weight of zinc, about 0.5 to $10 \times 10^{-3}$ parts by weight of manganese, about 0.1 to $4 \times 10^{-3}$ parts by weight of boron, about 1 to $20 \times 10^{-3}$ parts by weight of silicon, about 50 to $300 \times 10^{-6}$ parts by weight of chromium, or mixtures thereof. Another preferred embodiment of the invention further comprises about 100 to $1000 \times 10^{-3}$ parts by weight of glucosamine sulfate, about 100 to $1000 \times 10^{-3}$ parts by weight of vitamin C, and/or about 0.1 to $5 \times 10^{-3}$ parts by weight of fluoride. Preferably, the composition also further comprises a member selected from the group consisting of microcrystalline cellulose, stearic acid, croscarmellose sodium, magnesium stearate, silica, and mixtures thereof.

The components of this invention can be prepared as a solid emulsion system by first suspending the ingredients in 30°–45° C. water with high speed agitation then subjecting the resulting suspension to high pressure piston homogenization at a pressure of 1000–2000 psi. Total solids content is controlled to between 20 and 60% by weight and the homogenate is then spray dried to less than 10% moisture at a temperature of 70°–140° F. using a Niro or similar spray drying apparatus. Alternatively, the dehydrated emulsion can be prepared using vacuum drying or freeze drying technology.

The composition of the dried emulsion comprises the following elements:

| Ipriflavone Dry Emulsion | | |
|---|---|---|
| Component | Functionality | Formula Percent |
| 2DE–40DE Maltodextrin (corn, rice, potato, tapioca) | | 38–56% |
| Vegetable oil (soybean) with 50% Ipriflavone (1:1 blend) | | 34–60% |
| Sodium caseinate | Emulsification | 5.25%–10.5% |
| Dipotassium phosphate | Emulsification | 2.00%–10.5% |
| Mono and diglycerides (lecithin) | Emulsification | 2.50%–5.0% |

The dry emulsion will be added to other ingredients in the formula.

While the formula shown above is an example of one aspect of the present invention, other exemplary embodiments are also possible which provide the benefits of ipriflavone in emulsion form without requiring use of an oil or liquid dosage form.

DETAILED DESCRIPTION

Before the presently preferred compositions and methods are disclosed and described in further detail, it is to be understood that this invention is not limited to the particular provided examples, and it is to be appreciated that processes and materials that fall within the scope of the present invention may vary significantly from those specifically described herein. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

In describing and claiming the present invention, the following terminology will be used in accordance with the definitions set out below.

As used herein, the term "ipriflavone" preferably includes a class of bioflavonoids, and most preferably includes 7-isopropoxyisoflavone which is a particular bioflavonoid derivative. Bioflavonoids are benzo-gamma-pyrone derivatives found in most photosynthesizing cells. Flavonoids have many pharmacological activities and have been shown to be potent inhibitors of several enzymes. Ipriflavone is an isoflavone derivative first isolated in the late 1960's as a modulator of mitochondrial phosphorylation with growth promoting properties but is devoid of estrogenic activity in both animals and humans. See Reginster J L., Ipriflavone: pharmacological properties and usefulness in postmenopausal osteoporosis, Bone and Mineral 1993; 23:223–232; Ushiroyama T, Okamura S, Ikeda, A, et al., Efficacy of ipriflavone and 1-alpha vitamin D therapy for the cessation of vertebral bone loss, Int J Gynecol Obstet 1995; 48:283–8.

As used herein, "microcrystalline hydroxyapatite concentrate" (MCHC) preferably includes a concentrate of raw bone containing organic and inorganic matrix in microcrystalline structure providing a large surface area, which helps facilitate mineral absorption. Preferably, the MCHC contains a ratio of 25% protein (mostly collagen), 25% elemental calcium, and 12% phosphorus, with the remainder comprised of fat and other minerals. Preferred collagen is type I collagen, the predominant type of collagen found in bone, accompanied by a small quantity of type V collagen. The contents of the MCHC is preferably certified by analysis as is known in the art. Certification proving the material is approved for human consumption, such as a Certificate of Edible Origin from the Ministry of Agriculture and Fisheries which accompanies MCHC imported from New Zealand, is most preferred. Also preferably, lead is not present in levels higher than 0.8 µg per gram of MCHC product.

As used herein, "effective amount" means an amount of an active ingredient that is nontoxic but sufficient to provide the desired effect and performance at a reasonable benefit/risk ratio attending any dietary supplement. For example, an effective amount of ipriflavone is an amount sufficient to measurably decrease bone resorption, preferably in the range of about 10 to $600 \times 10^{-3}$ parts by weight and, more preferably, in the range of about 100 to $600 \times 10^{-3}$ parts by weight. By way of further example, an effective amount of vitamin D is an amount sufficient to maintain intracellular and extracellular calcium concentrations within a physiologically appropriate range for maintaining bone mass, preferably in the range of about 20 to 500 international units (IU) and, more preferably, in the range of about 50 to 300 international units. By way of still further example, an effective amount of a calcium source is an amount sufficient to maintain intracellular and extracellular calcium concentrations within a physiologically appropriate range, preferably in the range of about 100 to $5000 \times 10^{-3}$ parts by weight and, more preferably, in the range of about 1000 to $5000 \times 10^{-3}$ parts by weight. These effective amounts can be determined without undue experimentation by any person skilled in the art by following the guidelines set forth in this application.

As used herein, "tablets" are solid dosage forms containing active ingredients with or without suitable diluents and prepared either by compression or molding methods well known in the art. Tablets have been in widespread use since the latter part of the $19^{th}$ century and their popularity continues. Tablets remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of active ingredients present and the intended method of administration. They are divided into two general classes, (1) compressed tablets, and (2) molded tablets or tablet triturates. In addition to the active or therapeutic ingredient or ingredients, tablets may contain a number of inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Preferred amounts of lubricants range from about 0.1% by weight to about 5% by weight.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Synthetic flavors of almost any desired type are now available.

As used herein, "microcrystalline cellulose" means purified, partially depolymerized cellulose prepared by treating α-cellulose, obtained as a pulp from fibrous plant material, with mineral acids. E.g., U.S. Pat. No. 3,141,875. Microcrystalline cellulose is used as a tablet diluent and disintegrant. It is compressed into self-binding tablets that disintegrate rapidly when placed in water.

As used herein, "stearic acid" means a mixture of stearic acid ($C_{16}H_{36}O_2$=284.48) and palmitic acid ($C_{16}H_{32}O_2$=256.43), which together constitute not less than 90% of the total content, wherein the content of $C_{16}H_{36}O_2$ is not less than 40% of the total. Stearic acid is used as an enteric tablet coating and formulation aid.

As used herein, "magnesium stearate" means a compound of magnesium with a mixture of solid organic acids obtained from fats, and chiefly consists of variable proportions of magnesium stearate and magnesium palpitate. It is used as a pharmaceutical necessity (lubricant) in the manufacture of compressed tablets.

As used herein, "croscarmellose sodium" is a cross-linked carboxymethylcellulose sodium. Cross-linking reduces its water solubility and permits the material to swell and take up many times its weight in water without losing its fibrous integrity. It is useful as a tablet excipient.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

The present invention advantageously preferably includes ipriflavone (an isoflavonoid) together with calcium, vitamin D, and certain key minerals known to be important for the formation and retention of bone mass. As described herein, the compositions and methods of the present invention reduce or even reverse perimenopausal and postmenopausal bone loss or bone thinning due to osteoporosis or other metabolic disease states, which increase bone remodeling and resorption in both men and women.

A more detailed description of the present invention includes a nutritional composition which contains: (1) ipriflavone (7-isopropoxy-isoflavone), a naturally occurring isoflavone found in legumes that is now synthesized commercially (it acts on bone metabolism by inhibiting osteoclast activity and excessive bone resorption); (2) microcrystalline hydroxyapatite concentrate (MCHC) preferably derived from cold processed whole raw bovine bone from New Zealand to minimize the presence of lead and other contaminants; and (3) cholecalciferol (1α vitamin D), which plays a major role in maintaining intracellular and extracellular calcium concentrations within a physiologically appropriate range by regulating calcium and phosphorus metabolism in the intestine, neuromuscular junctions, and bone.

Microcrystalline hydroxyapatite is a preferred source of calcium for supplementation since it contains the entire organic matrix (native collagen and mucopolysaccharides) and minerals (phosphorus, magnesium, fluoride, zinc, silicon, manganese, and other trace minerals) in the same proportions as living bone and therefore provides all the nutrients needed for the formation of new bone in humans.

The advantages of ipriflavone have been reviewed above. Ipriflavone is an isoflavone derivative that inhibits bone resorption and promotes bone formation. Ipriflavone is used for treatment of osteoporosis, Paget's disease, and hyperparathyroidism—conditions of high bone turnover. See Reginster J L, Ipriflavone: pharmacological properties and usefulness in postmenopausal osteoporosis, Bone and Mineral 1993; 23:223–232. Safety of internal use of ipriflavone has been demonstrated in studies with consumption data of up to 2 years with adverse reactions equal to that observed during administration of a placebo. See Agnusdei D, Bufalino L, Efficacy of ipriflavone in established osteoporosis and long-term safety, Calcified Tissue International 1997; 61:S23–S27. Despite its structural similarity to some of the naturally occurring phytoestrogens, ipriflavone has been shown to be devoid of any estrogenic activity in animals and in humans and does not appear to modify secretion or metabolism of endogenous estrogens. See Melis G B, Paoletti A M, Cagnacci A, et al., Lack of any estrogenic effect of ipriflavone in postmenopausal women, J Endocrinol Invest 1992; 15:755–61.

It has been shown in animal research, see Valente M, Bufalino L, Castiglione G N, et al., Effects of 1-year treatment with ipriflavone on bone in postmenopausal women with low bone mass, Calcif Tissue Int 1994; 54:377–380, that ipriflavone reduces bone resorption by inhibiting the recruitment and differentiation of preosteoclasts in differentiated osteoclasts as well as providing a direct inhibitory effect on osteoclasts. In vitro studies demonstrate ipriflavone increases collagen synthesis and alkaline phosphatase activity by stimulating the growth and function of osteoblast-like cells. It has been proposed that ipriflavone inhibits the production of prostaglandin $E_2$ and may promote mitotic activity in and calcification of, osteoblasts.

It has been shown in numerous double-blind, placebo-controlled studies that ipriflavone reduces bone mineral loss and increases bone density in postmenopausal women with osteopenia or established osteoporosis. See Adami S, Bufalino L, Cervetti R, et al., 1priflavone prevents radial bone loss in postmenopausal women with low bone mass over 2 years, Osteoporosis Int 1997; 7:119–25; Valente M, Bufalino L, Castiglione G N, et al., Effects of 1-year treatment with ipriflavone on bone in postmenopausal women with low bone mass, Calcif Tissue Int 1994; 54:377–380; Agnusdei D, et al., Effects of ipriflavone on bone mass and calcium metabolism in postmenopausal osteoporosis, Bone Miner 1992; 19 (Suppl):S43–S48; Agnusdei D, Zacchei F, Bigazzi S, et al., Metabolic and clinical effects of ipriflavone in established postmenopausal osteoporosis, Drugs Exp Clin Res 1989 (XV)2:97–104; Agnusdei D, Bufalino L, Efficacy of ipriflavone in established osteoporosis and long-term safety, Calcified Tissue International 1997; 61:S23–S27; Kovacs A B, Efficacy of ipriflavone in the prevention and treatment of postmenopausal osteoporosis, Agents Actions 1994; 41:86–7. Therefore, in accordance with the present invention, significant positive effects are obtained by the addition of ipriflavone to a composition for use as a dietary supplement, including but not limited to: increase of calcium, phosphorus, and potassium retention in the body, inhibition of bone resorption, and increase in bone density with established osteoporosis.

Research with postmenopausal and ovariectomized human subjects examining the therapeutic affects of ipriflavone in combination with 1α vitamin D, see Ushiroyama T, Okamura S, Ikeda, A, et al., Efficacy of ipriflavone and 1-alpha vitamin D therapy for the cessation of vertebral bone loss, Int J Gynecol Obstet 1995; 48:283–8, demonstrates increased effectiveness in bone loss reduction after 18 months with this combined therapy. Vitamin D stimulates gastrointestinal absorption calcium leading to inhibition of PTH-mediated bone resorption, and directly acts on osteoblasts and indirectly on osteoclast in the regulation of bone remodeling. Bone mass density in postmenopausal women has shown to be directly correlated with serum vitamin $D_3$ ($25(OH)D_3$) levels and calcium absorption in the gastrointestinal tract. Reduced bone density in postmenopausal women is demonstrated to be an imbalance between bone resorption and bone formation resulting in high bone turnover. Ipriflavone inhibits bone resorption and enhances bone formation while 1α vitamin D increases gastrointestinal absorption and promotes bone mineralization. 1α Vitamin D and ipriflavone exhibit complementary physiological actions that have a synergist effect within the human body.

Adequate calcium intake throughout life, particularly for women during their first three decades when peak bone mass is achieved, is a significant factor in determining if osteoporosis will develop later in life. Additionally, adult women benefit from calcium supplementation even if peak bone mass has been attained at an earlier age. For menopausal women, a daily intake of 1000 mg of calcium is recommended. See Ruegsegger P, Keller A, Dambacher M A, Comparison of the treatment effects of ossein-hydroxyapatite compound and calcium carbonate in osteoporotic females, Osteo Int 1995; 5:30–34; Strause et al., The role of trace elements in bone metabolism, In: Nutritional Aspects of Osteoporosis. New York: Raven Press; 1991.

Research demonstrates that calcium sources vary in bioavailability and effectiveness in preventing bone loss. When compared to calcium carbonate, calcium in the form of MCHC was more effective in reducing peripheral trabecular bone loss in osteoporotic women. See Ruegsegger P, Keller A, Dambacher M A, Comparison of the treatment, effects of ossein-hydroxyapatite compound and calcium carbonate in osteoporotic females, Osteo Int 1995; 5:30–34. Other beneficial components in MCHC include hydroxyapatite, minerals, collagen, and non-collagenous proteins/peptides containing insulin-like growth factor I, insulin-like growth factor II, transforming growth factor beta, and osteocalcin. It has been determined that the absorption of calcium is enhanced in the presence of protein as is found in MCHC. Additionally, MCHC provides a large surface area that allows the minerals to be released from the organic matrix in the intestine. See Ruegsegger P, Keller A, Dambacher M A, Comparison of the treatment effects of ossein-hydroxyapatite compound and calcium carbonate in osteoporotic females, Osteo Int 1995; 5:30–34; Stepan J J, Mohan S, Jennings J C, et al., Quantitation of growth factors in ossein-mineral-compound. Life Sciences 1991; 49:79–84; Epstein 0, Kato Y, Dick R, Sherlock S, Vitamin D, hydroxyapatite, and calcium gluconate in treatment of cortical bone thinning in postmenopausal women with primary biliary cirrhosis, The American Journal of Clinical Nutrition 1982; 36:426–430. Animal research has shown significant improvements in the pattern and quality of bone healing with MCHC added to the diet when compared with MCHC ash or calcium carbonate. The beneficial effect of the MCHC is lost if the organic components of the compound are destroyed or if pure calcium carbonate is substituted. See Annefeld M, Caviezel R, Schacht E, Schicketanz K H, The influence of ossein-hydroxyapatite compound ('Ossopan') on the healing of a bone defect, Curr Med Res Opin 1986; 10:241–250. Other research with male and female patients with osteoporosis and/or skeletal pain found that MCHC dramatically reduced skeletal pain as well as produced favorable biochemical and radiological bone changes. See Pines A, Raafat H, Lynn A H, Whittington J, Clinical trial of microcrystalline hydroxyapatite compound ('Ossopan') in the prevention of osteoporosis due to corticosteroid therapy, Cur Med Res Opin 1984; 8:734–742.

The composition of the present invention can also include various minerals known to positively affect the health of bone. Such minerals include magnesium, copper, zinc, manganese, boron, fluoride, silicon, and chromium. These minerals can be present as pharmaceutically acceptable salts or, in some cases, as bioavailable chelates. The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric acids. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. In addition, some minerals can be provided in more bioavailable forms, such as amino acid chelates, which are well known in the art. U.S. Pat. No. 5,292,538. Examples of minerals that can be provided as amino acid chelates include calcium, magnesium, manganese, zinc, boron, copper, and chromium. Preferred magnesium salts and chelates include magnesium oxide, magnesium glycinate, magnesium citrate, magnesium aspartate, and magnesium malate, and mixtures thereof. Preferred copper salts and chelates include copper sulfate, copper oxide, copper glycinate, copper lysinate, copper tyrosinate, and copper gluconate, and mixtures thereof. Preferred zinc salts and chelates include zinc sulfate, zinc oxide, zinc ascorbate, zinc glycinate, zinc aspartate, zinc arginate, zinc citrate, zinc gluconate, and zinc picolinate, and mixtures thereof. Preferred manganese salts and chelates include manganese sulfate, manganese glycinate, manganese gluconate, manganese arginate, and manganese aspartate, and mixtures thereof. Preferred boron salts and chelates include boron citrate, boron aspartate, and boron glycinate, and mixtures thereof. Preferred fluoride salts include a neutral sodium fluoride and an acidulated phosphate fluoride, and mixtures thereof. Preferred silicon salts and chelates include silicon dioxide and Horse herb (*Equisetum arvense*), and mixtures thereof. Preferred chromium salts and chelates include dinicotinate glycinate, chromium aspartate, and chromium picolinate, and mixtures thereof.

Another preferred embodiment of the present invention further comprises glucosamine sulfate. The connective tissues are constantly subjected to stresses and strains from mechanical forces that can result in afflictions, such as arthritis, joint inflammation, and stiffness. Such afflictions are especially acute in joints, such as the neck, back, arms, hips, ankles, and feet. Indeed, connective tissue afflictions are quite common, presently affecting millions of Americans. Further, such afflictions can be not only painful, but can also be debilitating.

The connective tissues are naturally equipped to repair themselves by manufacturing and remodeling prodigious amounts of collagen and proteoglycans (the major components of connective tissues). This ongoing process is placed under stress when an injury occurs to connective tissues. In such cases, the production of connective tissue (along with collagen and proteoglycans) can double or triple over normal amounts, thereby increasing the demand for the building blocks of both collagens and proteoglycans. The building blocks for collagen are amino acids. Proteoglycans are large and complex macromolecules comprises mainly of long chains of modified sugars called glycosaminoglycans (GAGs) or mucopolysaccharides. Proteoglycans provide the framework for collagen to follow. They also hold water to give the connective tissues (especially cartilage) flexibility, resiliency, and resistance to compression. In the production of proteoglycans, the rate-limiting step is the conversion of glucose to glucosamine for the production of GAGs. Glucosamine, an aminosugar, is the key precursor to all the various modified sugars found in GAGs-glucosamine sulfate, galactosamine, N-acetylglucosamine, etc. Glucosamine also makes up 50% of hyaluronic acid, the backbone of proteoglycans, on which other GAGs, like chondroitin sulfates are added. The GAGs are then used to build proteoglycans and, eventually, connective tissue. Once glucosamine is formed, there is no turning away from the synthesis of GAGs and collagen.

Another preferred embodiment of the present invention further comprises vitamin C. Vitamin C, or ascorbic acid, is known to be essential for the formation of intercellular collagen. Symptoms of scurvy, due to vitamin C deficiency, include bleeding gums, easy bruising and a tendency toward bone fractures. All these symptoms are a result of the requirement for vitamin C in the development of the ground substance between our cells. This ground substance, primarily collagen, is the cement that gives our tissues form and substance. Collagens are principal components of tendons, ligaments, skin, bone, teeth, cartilage, heart valves, intervertebral discs, cornea, eye lens, in addition to the ground substance between cells. Some collagen forms in the absence of ascorbic acid, but the fibers are abnormal, resulting in skin lesions and blood vessel fragility, characteristics of scurvy. In scorbutic tissues the amorphous ground substance and the fibroblasts in the area between the cells appear normal but without the matrix of collagen fibers. These bundles of collagenous material appear within a few hours after administration of ascorbic acid. This points to the relationship of the vitamin in maintenance of tooth structures, matrix of bone, and the walls of capillaries. Vitamin C is essential for the healing of bone fractures. Such fractures heal slowly in a patient deficient in vitamin C. This is true also of wound healing.

Preferred formulations and ranges of these ingredients are:

| Minerals and Other Ingredients | Ranges in Parts by Weight | |
| --- | --- | --- |
| | Broad | Preferred |
| Magnesium | $50-400 \times 10^{-3}$ | $100-300 \times 10^{-3}$ |
| Copper | $0.04-5 \times 10^{-3}$ | $0.2-2 \times 10^{-3}$ |
| Zinc | $1-15 \times 10^{-3}$ | $1-10 \times 10^{-3}$ |
| Manganese | $0.5-10 \times 10^{-3}$ | $0.5-8 \times 10^{-3}$ |
| Boron | $0.1-4 \times 10^{-3}$ | $0.5-4 \times 10^{-3}$ |
| Silicon | $1-20 \times 10^{-3}$ | $1-10 \times 10^{-3}$ |
| Chromium | $50-300 \times 10^{-6}$ | $50-200 \times 10^{-6}$ |
| Fluoride | $0.1-5 \times 10^{-3}$ | $0.25-1 \times 10^{-3}$ |
| Glucosamine Sulfate | $100-1000 \times 10^{-3}$ | $100-500 \times 10^{-3}$ |
| Vitamin C | $100-1000 \times 10^{-3}$ | $100-500 \times 10^{-3}$ |

EXAMPLES

The following exemplary formulations represent specific embodiments of the invention. The composition of the present invention may be administered in tablet, powder, or emulsion form. Preferred dosages are about 0.007 g/kg per day to about 0.1 g/kg per day. In the preferred formulations set forth below, the formula components are specified by weight. Dosage quantities are per serving, with a-three serving daily recommendation.

Formulation A

| Component | Dosage per 2 tablets | Functionality | Example Specific Formulation | Formula % |
| --- | --- | --- | --- | --- |
| Microcrystalline hydroxyapatite | 1000 mg–5000 mg | Calcium source | 1000 mg | Approx. 55.55% |
| Cholecalciferol | 50 IU–300 IU | Source of vitamin D activity | 150 IU | Approx. 0.02% |
| Ipriflavone | 100 mg–600 mg | Isoflavone stimulates osteoblast activity | 100 mg | Approx. 5.55% |
| Dicalcium phosphate | 10 mg–1400 mg | Excipient and supplementary calcium source | 700 mg | Approx. 38.88% |

Excellent results were obtained using Formulation A.

Formulation B

| Component | Dosage per 2 tablets | Functionality | Example Specific Formulation | Formula % |
| --- | --- | --- | --- | --- |
| Microcrystalline | 1000 mg–5000 mg | Calcium source | 1000 mg | Approx. 55.55% |
| Cholecalciferol | 50 IU–300 IU | Source of vitamin D activity | 150 IU | Approx. 0.02% |
| Ipriflavone (*in dry emulsion form so adjust weight of emulsion activity accordingly) | | Isoflavone stimulates osteoblast | 100 mg* | Approx. 5.55% |

-continued

| Component | Dosage per 2 tablets | Functionality | Example Specific Formulation | Formula % |
|---|---|---|---|---|
| Dicalcium phosphate | 10 mg–1400 mg | Excipient and supplementary calcium source | 700 mg | Approx. 38.88% |

Excellent results were obtained using Formulation B.

Formulation C

| Component | Dosage per 2 tablets (rec. TID) | Functionality | Example Specific Formulation | Formula % |
|---|---|---|---|---|
| Microcrystalline hydroxyapatite | 1000 mg–5000 mg | Calcium source | 1000 mg | Approx. 47.61% |
| Cholecalciferol | 50 IU–300 IU | Source of vitamin D | 200 IU | Approx. 0.02% |
| Ipriflavone (*in dry emulsion form so adjust weight of emulsion accordingly) | 100 mg–600 mg | Isoflavone stimulates osteoblast | 200 mg* | Approx. 9.52% |
| Dicalcium phosphate | 100 mg–1400 mg | Excipient and supplementary calcium source | 700 mg | Approx. 33.33% |
| Magnesium salts and/or chelates (to include magnesium oxide, magnesium glycinate, magnesium citrate, magnesium aspartate, magnesium malate) | 50–400 mg | Essential for vitamin D activity; promotes bone formation | 200 mg | Approx. 9.52% |

Good results are obtained using Formulation C.

Formulation D

| Component | Dosage per 2 tablets (rec. TID) | Functionality | Example Specific Formulation | Formula % |
|---|---|---|---|---|
| Microcrystalline hydroxyapatite | 1000 mg–5000 mg | Calcium source | 1000 mg | Approx. 47.00% |
| Cholecalciferol | 50 IU–300 IU | Source of vitamin D activity | 200 IU | Approx. 0.02% |
| Ipriflavone (*in dry emulsion form so adjust weight of emulsion accordingly) | 100 mg–600 mg | Isoflavone stimulates osteoblast activity | 200 mg* | Approx. 9.55% |
| Dicalcium phosphate | 100 mg–1400 mg | Excipient and supplementary calcium source | 700 mg | Approx. 33.23% |
| Magnesium salts and/or chelates (to include magnesium oxide, magnesium glycinate, magnesium citrate, magnesium aspartate, magnesium malate) | 50 mg–400 mg | Essential for vitamin D activity; promotes bone formation | 200 mg | Approx. 9.55% |
| Copper salts and/or chelates (to include copper sulfate, copper oxide, copper glycinate, copper lysinate, copper tyrosinate, copper gluconate) | 0.04 mg–5 mg | Provides a key catalytic function supporting the cross-linking of collagen and elastin in the organic bone matrix | 0.67 mg | Approx. 0.03% |
| Zinc salts and/or chelates (to include zinc sulfate, zinc oxide, zinc ascorbate, zinc glycinate, zinc aspartate, zinc arginate, zinc citrate, zinc gluconate, zinc picolinate) | 1 mg–15 mg | Supports osteoblastic activity, collagen, and enzymes important in bone formation | 4.0 mg | Approx. 0.19% |
| Manganese salts or chelates (to include manganese sulfate, manganese glycinate, manganese gluconate, manganese arginate, manganese aspartate, manganese) | 0.5 mg–10 mg | Provides catalytic support to enzymes involved in bone formation | 1.2 mg | Approx. 0.057% |

Good results are obtained using Formulation D.

Formulation E

| Component | Dosage per 2 tablets (rec. TID) | Functionality | Example Specific Formulation | Formula % |
|---|---|---|---|---|
| Microcrystalline hydroxyapatite | 1000 mg–5000 mg | Calcium source | 1000 mg | Approx. 47.44% |
| Cholecalciferol | 50 IU–300 IU | Source of vitamin D activity | 200 IU | Approx. 0.02% |
| Ipriflavone (*in dry emulsion form so adjust weight of emulsion accordingly) | 100 mg–600 mg | Isoflavone stimulates osteoblast | 200 mg* | Approx. 9.49% |
| Dicalcium phosphate | 100 mg–1400 mg | Excipient and supplementary calcium source | 700 mg | Approx. 33.21% |
| Magnesium salts and/or chelates (to include magnesium oxide, magnesium glycinate, magnesium citrate, magnesium aspartate, | 50 mg–400 mg | Essential for vitamin D activity; promotes bone formation | 200 mg | Approx. 9.49% |

-continued

| Component | Dosage per 2 tablets (rec. TID) | Functionality | Example Specific Formulation | Formula % |
|---|---|---|---|---|
| magnesium malate) | | | | |
| Copper salts and/or chelates (to include copper sulfate, copper oxide, copper glycinate, copper lysinate, copper tyrosinate, copper gluconate) | 0.04 mg– 5 mg | Provides a key catalytic function supporting the cross-linking of collagen and elastin in the organic bone matrix | 0.67 mg | Approx. 0.03% |
| Zinc salts and/or chelates (to include zinc sulfate, zinc oxide, zinc ascorbate, zinc glycinate, zinc aspartate, zinc arginate, zinc citrate, zinc gluconate, zinc picolinate) | 1 mg– 15 mg | Supports osteoblastic activity, collagen, and enzymes important in bone formation | 4.0 mg | Approx. 0.19% |
| Manganese salts or chelates (to include manganese sulfate, manganese glycinate, manganese gluconate, manganese arginate, manganese aspartate, manganese) | 0.5 mg– 10 mg | Provides catalytic support to enzymes involved in bone formation | 1.2 mg | Approx. 0.057% |
| Boron as chelate (boron citrate, boron aspartate, boron glycinate) | 0.1 mg– 4 mg | Involved in the maintenance of calcium balance | 1.5 mg | Approx. 0.071% |

Good results are obtained using Formulation E.

Formulation F

| Component | Dosage per 2 tablets (rec. TID) | Functionality | Example Specific Formulation | Formula % |
|---|---|---|---|---|
| Microcrystalline hydroxyapatite | 1000 mg– 5000 mg | Calcium source | 1000 mg | Approx. 47.43% |
| Cholecalciferol | 50 IU– 300 IU | Source of vitamin D activity | 200 IU | Approx. 0.02% |
| Ipriflavone (*in dry emulsion form so adjust weight of emulsion accordingly) | 100 mg– 600 mg | Isoflavone stimulates osteoblast activity | 200 mg* | Approx. 9.49% |
| Dicalcium phosphate | 100 mg– 1400 mg | Excipient and supplementary calcium source | 700 mg | Approx. 33.20% |
| Magnesium salts and/or chelates magnesium oxide, magnesium glycinate, magnesium citrate, | 50 mg– 400 mg | Essential for vitamin D activity; promotes bone formation | 200 mg | Approx. 9.49% |

-continued

| Component | Dosage per 2 tablets (rec. TID) | Functionality | Example Specific Formulation | Formula % |
|---|---|---|---|---|
| magnesium aspartate, magnesium malate) | | | | |
| Copper salts and/or copper chelates (to include copper sulfate, oxide copper glycinate, copper lysinate, copper tyrosinate, copper gluconate) | 0.04 mg– 5 mg | Provides a key catalytic function supporting the cross-linking of collagen and elastin in the organic bone matrix | 0.67 mg | Approx. 0.03% |
| Zinc salts and/or chelates (to include zinc sulfate, zinc oxide, zinc ascorbate, zinc glycinate, zinc aspartate, zinc arginate, zinc citrate, zinc gluconate, zinc picolinate) | 1 mg– 15 mg | Supports osteoblastic activity, collagen, and enzymes important in bone formation | 4.0 mg | Approx. 0.19% |
| Manganese salts or chelates (to include manganese sulfate, manganese glycinate, manganese gluconate, manganese arginate, manganese aspartate, manganese) | 0.5 mg– 10 mg | Provides catalytic support to enzymes involved in bone formation | 1.2 mg | Approx. 0.06% |
| Boron as chelate (boron citrate, boron aspartate, boron glycinate) | 0.1 mg– 4 mg | Involved in the maintenance of calcium balance | 1.5 mg | Approx. 0.07% |
| Fluoride (a neutral sodium fluoride or acidulated phosphate fluoride) | 0.25 mg– 1 mg | Stimulates osteoblast activity | 0.55 mg | Approx. 0.03% |

Good results are obtained using Formulation F.

Formulation G

| Component | Dosage per 2 tablets (rec. TID) | Functionality | Example Specific Formulation | Formula % |
|---|---|---|---|---|
| Microcrystalline hydroxyapatite | 1000 mg– 5000 mg | Calcium source | 1000 mg | Approx. 47.38% |
| Cholecalciferol | 50 IU– 300 IU | Source of vitamin D activity | 200 IU | Approx. 0.02% |
| Ipriflavone (*in dry emulsion form so adjust weight of emulsion accordingly) | 100 mg– 600 mg | Isoflavone stimulates osteoblast activity | 200 mg* | Approx. 9.48% |
| Dicalcium phosphate | 100 mg– 1400 mg | Excipient and calcium source | 700 mg | Approx. 33.16% |
| Magnesium salts | 50 mg– | Essential for | 200 mg | Approx. |

-continued

| Component | Dosage per 2 tablets (rec. TID) | Functionality | Example Specific Formulation | Formula % |
|---|---|---|---|---|
| and/or chelates (to include magnesium oxide, magnesium glycinate, magnesium citrate, magnesium aspartate, magnesium malate) | 400 mg | vitamin | | 9.48% |
| Copper salts and/or chelates (to include copper sulfate, copper oxide, copper glycinate, copper lysinate, copper tyrosinate, copper gluconate) | 0.04 mg–5 mg | Provides catalytic function supporting the cross-linking of collagen and elastin in the organic bone matrix | 0.67 mg | Approx. 0.03% |
| Zinc salts and/or chelates (to include zinc sulfate, zinc oxide, zinc ascorbate, zinc glycinate, zinc aspartate, zinc arginate, zinc citrate, zinc gluconate, zinc picolinate) | 1 mg–15 mg | Supports osteoblastic activity, collagen, enzymes important in bone formation | 4.0 mg | Approx. 0.19% |
| Manganese salts or chelates (to include manganese sulfate, manganese glycinate, manganese gluconate, manganese arginate, manganese aspartate, manganese) | 0.5 mg–10 mg | Provides catalytic support to enzymes involved in bone formation | 1.2 mg | Approx. 0.06% |
| Boron as chelate (boron citrate, boron aspartate, boron glycinate) | 0.1 mg–4 mg | Involved in the maintenance of calcium balance | 1.5 mg | Approx. 0.07% |
| Silicon as salt or chelate (silicon dioxide, *Equistetum arvense*—Horse Herb | 1.0 mg–20 mg | Involved in bone calcification | 3.0 mg | Approx. 0.14% |

Good results are obtained using Formulation G.

Formulation H

| Component | Dosage per 2 tablets (rec. TID) | Functionality | Example Specific Formulation | Formula % |
|---|---|---|---|---|
| Microcrystalline hydroxyapatite | 1000 mg–5000 mg | Calcium source | 1000 mg | Approx. 40.92% |
| Cholecalciferol | 50 IU–300 IU | Source of vitamin D activity | 200 IU | Approx. 0.02% |
| Ipriflavone (*in dry emulsion | 100 mg–600 mg | Isoflavone stimulates | 200 mg* | Approx. 8.18% |

-continued

| Component | Dosage per 2 tablets (rec. TID) | Functionality | Example Specific Formulation | Formula % |
|---|---|---|---|---|
| form so adjust weight of emulsion accordingly) | | osteoblast activity | | |
| Dicalcium phosphate | 100 mg–1400 mg | Excipient and supplementary calcium source | 700 mg | Approx. 28.64% |
| Magnesium salts and/or chelates (to include magnesium oxide, magnesium glycinate, magnesium citrate, magnesium aspartate, magnesium malate) | 50 mg–400 mg | Essential for vitamin D activity; promotes bone formation | 200 mg | Approx. 8.18% |
| Copper salts and/or chelates (to include copper sulfate, copper oxide, copper glycinate, copper lysinate, copper tyrosinate, copper gluconate) | 0.04 mg–5 mg | Provides a key catalytic function supporting the cross-linking of collagen and elastin in the organic bone matrix | 0.67 mg | Approx. 0.03% |
| Zinc salts and/or chelates (to include zinc sulfate, zinc oxide, zinc ascorbate, zinc glycinate, zinc aspartate, zinc arginate, zinc citrate, zinc gluconate, zinc picolinate) | 1 mg–15 mg | Supports osteoblastic activity, collagen, and enzymes important in bone oxide, zinc formation | 4.0 mg | Approx. 0.16% |
| Manganese salts or chelates (to include manganese sulfate, manganese glycinate, manganese gluconate, manganese arginate, manganese aspartate, manganese) | 0.5 mg–10 mg | Provides catalytic support to enzymes involved in bone formation | 1.2 mg | Approx. 0.05% |
| Boron as chelate (boron citrate, boron aspartate, boron glycinate) | 0.1 mg–4 mg | Involved in the maintenance of calcium balance | 1.5 mg | Approx. 0.06% |
| Silicon as salt or chelate (silicon dioxide, *Equistetum arvense*—Horse Herb | 1.0 mg–20 mg | Involved in bone calcification | 3.0 mg | Approx. 0.12% |
| Glucosamine sulfate | 100 mg–1000 mg | Potentiate glycosaminoglycan synthesis which stimulates | 167 mg | Approx. 6.83% |

-continued

| Component | Dosage per 2 tablets (rec. TID) | Functionality | Example Specific Formulation | Formula % |
|---|---|---|---|---|
| | | collagen and matrix synthesis | | |
| Chromium as chelate (dinicotinate glycinate, chromium aspartate, chromium picolinate) | 50 mcg–300 mcg | Improves insulin metabolism, a key hormone for cell replication | 80 mcg | Approx. 0.0003% |
| Vitamin C (Ultra Potent-C ®, Ester-C, ascorbic acid, calcium ascorbate, sodium ascorbate) | 100–1000 mg | Essential for the synthesis of collagen | 167 mg | Approx. 6.83% |

Good results are obtained using Formulation H.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A composition for benefiting human bone health, comprising an effective amount of a calcium source; an effective amount of a source of vitamin D activity comprising cholecalciferol present in the range from about 50 IU to about 300 IU; and an effective amount of ipriflavone.

2. The composition of claim 1, wherein th calcium source comprises microcrystalline hydroxyapatite.

3. The composition of claim 1, wherein ipriflavone is in dry emulsion form.

4. The composition of claim 1, wherein ipriflavone is present in the range from about 100 mg to about 600 mg.

5. The composition of claim 1, further comprising an ingredient selected from the group consisting of a magnesium source, a silicon ingredient, a boron ingredient, and glucosamine sulfate.

6. The composition of claim 1, further comprising magnesium.

7. The composition of claim 6, wherein the magnesium is in the form of magnesium citrate.

8. The composition of claim 6, wherein the magnesium is in the form of magnesium oxide.

9. The composition of claim 7, wherein the magnesium is in the form of magnesium citrate and magnesium oxide.

10. The composition of claim 1, further comprising boron.

11. The composition of claim 10, wherein the boron is in the form of boron citrate.

12. The composition of claim 1, further comprising an ingredient selected from the group consisting of a copper ingredient, a zinc ingredient, a manganese ingredient, a chromium ingredient, and a vitamin C ingredient.

13. A method for supplementing a diet for benefiting human bone health comprising administering at least one daily serving of a composition comprising: an effective amount of a calcium source; an effective amount of source of vitamin D activity comprising cholecalciferol present in the range from about 50 IU to about 300 IU; and an effective amount of ipriflavone.

14. The method of claim 13, wherein the calcium source comprises microcrystalline hydroxyapatite.

15. The method of claim 13, wherein the ipriflavone is in dry emulsion form.

16. The method of claim 13, wherein the ipriflavone is present in the range from about 100 mg to about 600 mg.

17. The method of claim 13, further comprising an ingredient selected from the group consisting of a magnesium source, a silicon ingredient, a boron ingredient, and glucosamine sulfate.

18. The method of claim 13, further comprising magnesium.

19. The method of claim 18, wherein the magnesium is in the form of magnesium citrate.

20. The method of claim 18, wherein the magnesium is in the form of magnesium oxide.

21. The method of claim 18, wherein the magnesium is in the from of magnesium citrate and magnesium oxide.

22. The method of claim 13, further comprising boron.

23. The method of claim 22, wherein the boron is in the form of boron citrate.

24. The method of claim 13, further comprising an ingredient selected from the group consisting of a copper ingredient, a zinc ingredient, a manganese ingredient, a chromium ingredient, and a vitamin C ingredient.

* * * * *